US010500134B2

(12) United States Patent  
Carrez et al.

(10) Patent No.: US 10,500,134 B2  
(45) Date of Patent: Dec. 10, 2019

(54) DEVICE FOR INTERFACING A VIAL TO BE PERFORATED

(71) Applicant: Vygon, Ecouen (FR)

(72) Inventors: Jean-Luc Carrez, Ecouen (FR); Jean-Louis Coussegal, Beauchamp (FR); Laurent Barre, Ecouen (FR); Isabelle Algrain, Puiseux en France (FR)

(73) Assignee: Vygon (FR)

( * ) Notice: Subject to any disclaimer, the term of this patent is extended or adjusted under 35 U.S.C. 154(b) by 353 days.

(21) Appl. No.: 15/029,436

(22) PCT Filed: Oct. 16, 2014

(86) PCT No.: PCT/EP2014/072181  
§ 371 (c)(1),  
(2) Date: Apr. 14, 2016

(87) PCT Pub. No.: WO2015/055751  
PCT Pub. Date: Apr. 23, 2015

(65) Prior Publication Data  
US 2016/0262981 A1 Sep. 15, 2016

(30) Foreign Application Priority Data  
Oct. 16, 2013 (FR) ..................... 13 60084

(51) Int. Cl.  
*A61J 1/20* (2006.01)  
*A61J 1/14* (2006.01)  
(Continued)

(52) U.S. Cl.  
CPC .......... *A61J 1/2048* (2015.05); *A61J 1/1406* (2013.01); *A61J 1/2096* (2013.01);  
(Continued)

(58) Field of Classification Search  
CPC .......................................... A61J 1/2048–2075  
See application file for complete search history.

(56) References Cited

U.S. PATENT DOCUMENTS

2007/0032775 A1  2/2007  Niedospial et al.  
2007/0244466 A1* 10/2007  Fangrow ............... A61J 1/2089  
604/411

(Continued)

FOREIGN PATENT DOCUMENTS

EP  0126718 A2  11/1984  
FR  1051136 A  1/1954  
(Continued)

OTHER PUBLICATIONS

FR 2951638 Machine Translation.*

(Continued)

*Primary Examiner* — Benjamin J Klein  
(74) *Attorney, Agent, or Firm* — Lerner, David, Littenberg, Krumholz & Mentlik, LLP (57) ABSTRACT

The invention relates to an interfacing device for establishing a connection between a fluid-injection instrument and a flask, said device comprising: fluid flow means configured such as to open into the flask to be perforated when the interfacing device is attached to the flask to be perforated; and a distal opening allowing the flow of gases and a proximal opening allowing the flow of liquids.

10 Claims, 8 Drawing Sheets

(51) Int. Cl.
*A61M 5/32* (2006.01)
*A61J 1/06* (2006.01)

(52) U.S. Cl.
CPC ............ *A61M 5/3202* (2013.01); *A61J 1/065* (2013.01); *A61J 1/1481* (2015.05); *A61J 1/1487* (2015.05); *A61J 1/201* (2015.05); *A61J 1/2075* (2015.05)

(56) References Cited

U.S. PATENT DOCUMENTS

| | | |
|---|---|---|
| 2011/0004183 A1 | 1/2011 | Carrez et al. |
| 2012/0078179 A1 | 3/2012 | Finke |
| 2014/0283948 A1 | 9/2014 | Algrain et al. |

FOREIGN PATENT DOCUMENTS

| | | | |
|---|---|---|---|
| FR | 2928539 A1 | 9/2009 | |
| FR | 2951638 A1 | 4/2011 | |
| FR | 2951648 A1 | 4/2011 | |
| FR | 2951638 B1 * | 5/2012 | ............ A61J 1/2096 |
| FR | 2982484 A1 | 5/2013 | |
| WO | 9720536 A1 | 6/1997 | |
| WO | 9720636 A1 | 6/1997 | |
| WO | 2007120641 A2 | 10/2007 | |

OTHER PUBLICATIONS

International Search Report for Application No. PCT/EP2014/072181 dated Jan. 23, 2015.

French Preliminary Search Report for Application No. FR1360084 dated Jul. 11, 2014.

* cited by examiner

DEVICE FOR INTERFACING A VIAL TO BE PERFORATED

CROSS REFERENCE TO RELATED APPLICATIONS

The present application is a national phase entry under 35 U.S.C. § 371 of International Application No. PCT/EP2014/072181, filed Oct. 16, 2014, which claims priority from French Patent Application No. 1360084, filed Oct. 16, 2013, the disclosures of which are incorporated by reference herein.

FIELD OF THE INVENTION

The invention relates to an interfacing device intended for establishing a connection between a fluid-injection instrument such as a syringe and a vial to be perforated containing a drug for purposes of preparing fluids intended to be infused in a patient.

TECHNOLOGICAL BACKGROUND

In oncology, for treating cancer tumors, it is necessary to infuse fluids which may be very aggressive. The preparation of these fluids, which appear as a solute, may prove to be dangerous for the caregiver in so far that they are very aggressive and may be the source of accidents with toxic or allergic effects. In many cases, the drug which has to be administered appears in the form of powder in a vial in vacuo, which is obturated by a plug with an elastomeric membrane.

In order to mix this drug contained in such a vial in vacuo to a fluid intended to be infused, in a first phase the drug has to be diluted as a powder in this liquid by means of a syringe generally equipped with a needle. The fluid to be infused may for example be saline (distilled water+NaCl).

The plug with an elastomeric membrane of the vial is then crossed with the needle, which has the effect of causing sudden entry of air into the vial which was in vacuo. This air mixes with the drug as a powder and may partly emerge therefrom by carrying away the pure drug, which is dangerous for the caregiver responsible for the preparation. Once the needle of the syringe has been put into place through the plug with an elastomeric membrane, the caregiver responsible for the preparation pushes by means of the syringe the fluid to be infused into the vial, which there again causes the initially confined air to emerge in the vial loaded if required with still not yet diluted drug particles.

The vial is then shaken and the mixture is sucked up through the plug with an elastomeric membrane by means of the syringe. In practice, the liquid mixture to be infused plus the diluted drug is injected and sucked up several times in succession out and into the vial with the syringe, in order to thoroughly mix the drug in the liquid. However, such a mixture causes inflows and outflows of air from the vial, which implies risks of pollution for the caregiver responsible for the preparation on the one hand and for the prepared mixture on the other hand.

Finally, the needle is taken out of the vial. It then has to be disconnected from the syringe without pricking anybody and avoiding any direct contact of the thereby produced mixture with the caregiver responsible for the preparation. The filled syringe is then connected near the patient to an infusion bag connected to the latter or directly connected to the actual patient.

During this handling, the main causes of an accident are related to sealing problems towards liquids and gases from the inside of the vial towards the outer medium, with dissemination of dangerous products, which may come into contact with the skin, the eyes and the respiratory system of the preparation and care personnel, but also to sealing problems of the outer medium towards the inside of the vial which risk contaminating the preparation, or further to problems of vertical stability of the interfacing device. It may prove to be necessary that the preparation personnel operate in confined spaces, under a hood or in enclosures, and with thick gloves.

Such interfacing devices are already known. For example, document FR 2 928 539 proposes an interfacing device comprising air circulation means, intended to allow inflows and outflows of air from the vial to be perforated, provided with air filtration means adapted for retaining the pure drug particles still not diluted during the air outflow from the vial, as well as of impurities contained in the ambient air penetrating into the vial upon air inflow into the vial. The device therefore gives the possibility of making the handling safe and preparing the mixture.

However, the use of this device causes several inflows and outflows of air into the vial which further pose safety problems. Indeed, the filtration means, which is generally in the form of an escape filter, is highly sensitive to liquids and its filtering does not seem to be sufficiently efficient for the users.

Moreover, the device is relatively complex to make and comprises a large number of parts.

In document FR 2 951 648, an interfacing device is therefore proposed, comprising a base on which is attached an air tank via air circulation means, in which the air tank comprises a rigid cell associated with a flexible membrane, defining a compartment isolated from the outside world. This improved air circulation system then replaces the filter and allows circulation of air in the vial, while maintaining the vial isolated from the outside and therefore risks of contamination by outer elements.

Such an interfacing device has good functionalities and gives the possibility of efficiently limiting the risks of contamination. However, its design is highly expensive and complex. Moreover, this design does not give the possibility of sampling the whole of the fluids in the vial.

Subsequently, in document FR 2 982 484 a more stable interfacing device was proposed in all the positions and during handling operations. This device retains the closed air circulation system but proposes another means for attaching the base to the vial through a hooking-up means of the harpoon type rather than a snap-on plug. For this, FR 2 982 484 proposes an interfacing device intended to establish a connection between a fluid-injection instrument and a vial to be perforated, comprising:

a suitable base for connecting the interfacing device to the fluid-injection instrument, a means for attaching the base on the vial to be perforated, arranged at a distal end of the interfacing device, having a divergent proximal end forming a shoulder and a suitable convergent distal end for facilitating penetration of the attachment means into the vial to be perforated, wherein the attachment means comprises at least one notch in an area adjacent to its proximal end suitable for establishing a fluidic communication between the vial to be perforated and an external space of the interfacing device.

This device clearly improves the ergonomics of the device. However, its design remains relatively expensive and complex.

In document WO 2007/120641 an interfacing device has also been proposed, comprising a base configured so as to be connected to an injection instrument on the one hand and to a vial to be perforated on the other hand. However, the device described in this document is very complex to apply, insofar that it proposes the introduction of a sachet into the vial during the perforation in order to compensate for pressure differences. The presence of such a sachet in the vial however risks disturbing the operator during successive suctions and re-injections for mixing the contents of the vial with the fluid, preventing the full taking up of the fluid and possibly having sealing problems.

Document WO 97/20536 as for it describes a device for preparing a drug solution reconstituted from two components. However, in this document, the pressure differences are compensated by means of a particle filter which, as this has been seen above, is highly sensitive to liquids and is not sufficiently efficient in the eyes of the users.

SUMMARY OF THE INVENTION

An object of the injection is therefore to propose an interfacing device which is ergonomic for an operator, facilitates the handling operations for attaching, mixing and sucking up fluid, notably in the field of oncology, while limiting the risks of contamination of the operator, whether this is from the vial towards the outside or from the outside towards the vial and giving the possibility of taking up a larger volume of fluid regardless of the volume of the vial to be perforated.

For this, the invention proposes an interfacing device intended to establish a connection between a fluid-injection instruction and a vial to be perforated, comprising:
  a base comprising:
    a first conduit, suitable for being attached to the vial to be perforated,
    a second conduit, suitable for allowing circulation of gases in the vial to be perforated, and
    a third conduit, suitable for being connected to the fluid-injection instrument,
  means for circulating fluids, comprising a proximal orifice in fluidic communication with the third conduit,
  the interfacing device being characterized in that the means for circulating fluids further comprise a tube, housed in the second conduit and translationally movable in said second conduit, and comprising at its distal end a distal orifice in fluidic communication with the second conduit, the proximal orifice and the distal orifice being configured so as to open into the vial to be perforated when the interfacing device is attached to said vial to be perforated.

Certain preferred but non-limiting features of this interfacing device are the following:
  the means for circulating fluids comprise an end piece, attached at a distal end of the first conduit of the base, said end piece comprising at its proximal end the proximal orifice,
  the tube is housed in the end piece and is translationally movable in said end piece,
  the distal end of the tube is flared,
  the proximal orifice extends laterally relatively to an extension direction of the tube,
  the proximal orifice is formed at a proximal end of the end piece,
  a distal end of the end piece is pointed,
  a proximal end of the tube is attached on a gas-exchange device,
  the device further comprises a sleeve positioned in the second conduit and suitable for sealably maintaining the tube in said second conduit,
  the device further comprises a protective member, attached on the first conduit and suitable for being attached to the vial to be perforated, and
  the first conduit and the second conduit are coaxial, the third conduit forming an angle comprised between 30° and 60° with the second conduit.

SHORT DESCRIPTION OF THE DRAWINGS

Other features, objects and advantages of the present invention will become better apparent upon reading the detailed description which follows, and with reference to the appended drawings given as non-limiting examples and wherein.

DETAILED DESCRIPTION OF AN EMBODIMENT

Now, we shall describe an interfacing device 1 with reference to the appended figures.

An interfacing device 1 intended to establish a connection between a fluid-injection instrument 2 and a vial to be perforated 3, comprises:
  a base 20 comprising:
    a first conduit 21, adapted to be attached to the vial to be perforated 3,
    a second conduit 22 suitable for allowing circulation of gases in the vial to be perforated 3, and
    a third conduit 23, suitable for being connected to the fluid-injection instrument 2,
  means for circulating fluids 10, 40, configured as so to open into the vial to be perforated 3 when the interfacing device 1 is attached to the vial to be perforated 3.

The means 10, 40 for circulating fluids comprise a distal orifice 42, in fluidic communication with the second conduit 22, and a proximal orifice 11 in fluidic communication with the third conduit 23, the proximal orifice 11 and the distal orifice 42 being configured so as to open into the vial to be perforated 3 when the interfacing device 1 is attached to said vial to be perforated 3.

The interfacing device 1 is intended to be mounted on the vial to be perforated 3 at a distal end 21*b* of the first conduit 21 and on the fluid-injection instrument 2, such as for example a syringe (not shown in the figures) at a proximal end 23*a* of the third conduit 23.

Any usual connection means between the fluid-injection instrument 2 and the base 20 may be used. Preferably, connection means will be selected, able to limit the risks of forming drops and easily cleanable, insofar that the obtained drugs risk being harmful for the operator. Typically, the fluid-injection instrument 2 which may be connected to the base 3 may comprise a syringe without any needle, such as the device described in document FR 10 51136 in the name of the Applicant.

The Base

The base 20 comprises a Y-shaped body comprising the first 21, second 22 and third 23 conduits.

The first conduit 21 extends along a first main axis X1 of the base 20 and is adapted so as to be sealably connected at its distal end 21*b* to the vial to be perforated.

The second conduit 22 extends along a second axis X2 from a proximal end 22*a* of the base 20 and is adapted for allowing circulation of gases from the vial to be perforated 3. For example, a tank 31 may be connected to the second conduit 22 in order to form a closed circuit for the gas initially contained in the vial to be perforated 3 and/or the tank 31.

In the exemplary embodiment illustrated in the figures, the second axis X2 and the first axis X1 are substantially parallel. For example, the second conduit 22 may extend in the extension of the first conduit 21, the first axis X1 and the second axis X2 then coinciding with each other.

Moreover, the first conduit 21 and the second conduit 22 are in fluidic communication.

The third conduit 23, as for it, extends along a third axis X3 from the base 20 and comprises a proximal end 23*a* suitable for receiving the fluid-injection device 2. For example, the proximal end 23*a* may comprise a screwing means of the Luer or Luer Lock type. The internal section of the third conduit 23 may notably be reduced at its intersection 23*b* with the first 21 and/or the second 22 conduit, in order to facilitate the injection and suction of the fluids in the vial to be perforated 3. Optionally, the proximal end 23*a* of the third conduit 23 may be obturated with a membrane (not shown in the figures) for sealing the third conduit 23 while allowing the connection of a fluid-injection device 2 such as a syringe.

Figure 5:
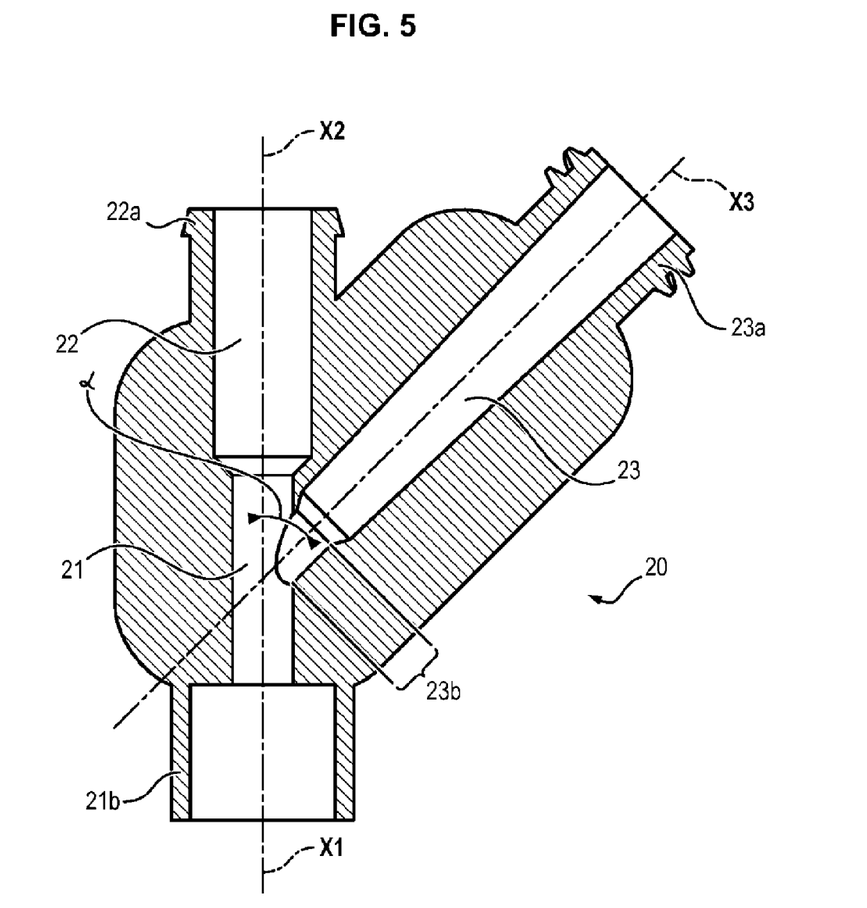
FIG. 5 illustrates a sectional view of the base of the interfacing device of FIG. 1.

The third axis X3 is preferably tilted relatively to the first axis X1 and to the second axis X2. Thus, in the exemplary embodiment illustrated in the figures, the third axis X3 forms an angle α comprised between 0° and 90° with the second axis X2, preferably between 30° and 60° (FIG. 5). As this will be seen subsequently, this tilt of the third conduit 23 relatively to the first and second conduits 21, 22 gives the possibility of improving the ergonomics of the interfacing device 1 upon introducing and sucking up fluids in the vial to be perforated 3.

Means for Circulating Fluids

The means for circulating fluids 10, 40 are adapted so as to allow the introduction and suction of a fluid in the vial to be perforated 3 by means of the fluid-injection device 2 on the one hand and the circulation of the gases (inflows and outflows) from the vial to be perforated 3, on the other hand.

For this purpose, the means for circulating fluids comprise a distal orifice 42, in fluidic communication with the second conduit 22, intended to allow circulation of the gases from the vial to be perforated 3, and a proximal orifice 11, in fluidic communication with the third conduit 23, intended to allow injection and suction of fluid by means of the injection device 2.

Figure 1:
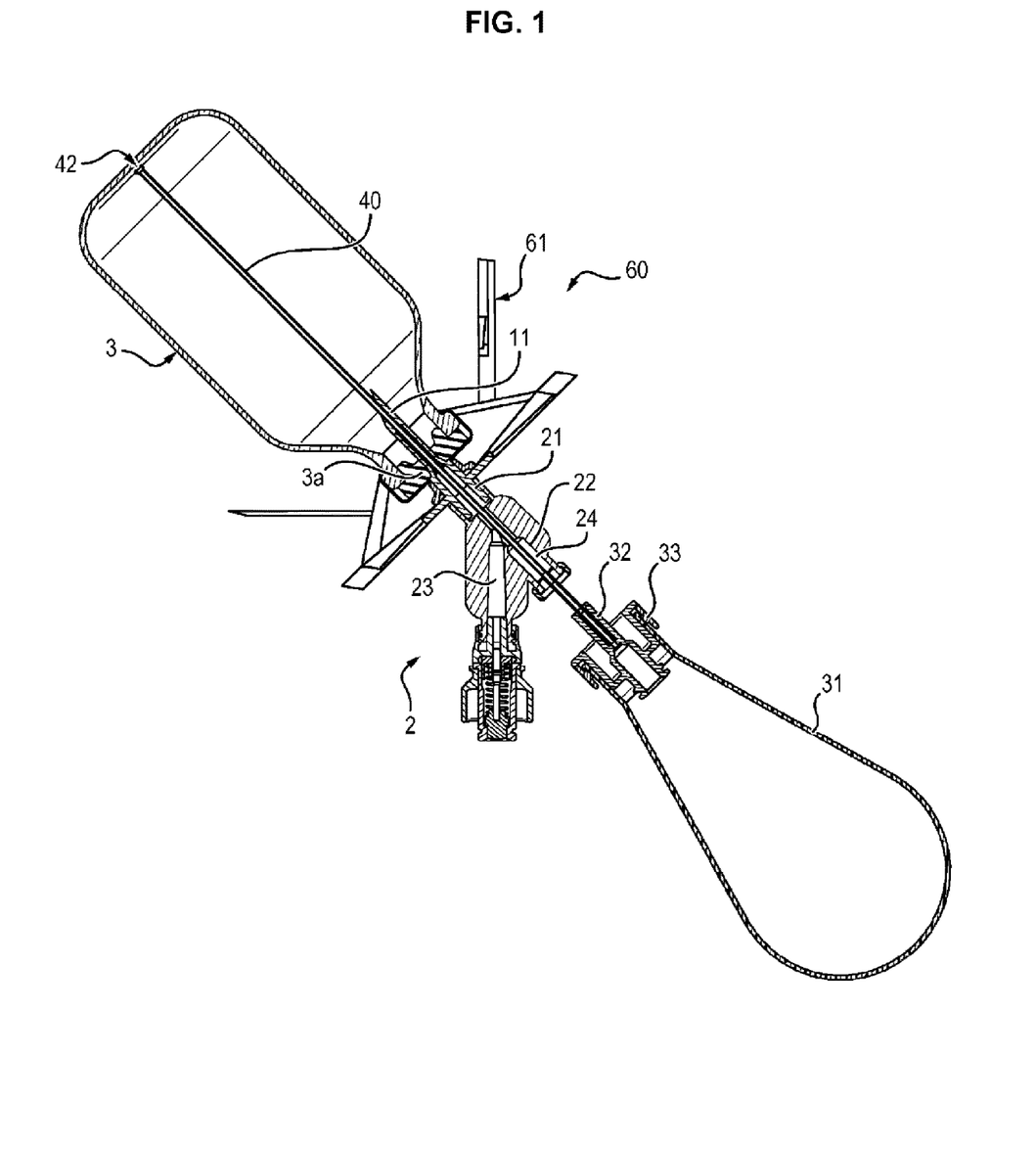
FIG. 1 is a sectional view in a turned-over position of a first embodiment of an interfacing device according to the invention attached on an exemplary vial to be perforated, and on which an exemplary interfacing device has been attached.

Advantageously, the positioning in the distal portion of the orifice 42 allowing circulation of the gases and the positioning in the proximal portion of the orifice 11 allowing circulation of the fluids (liquids) give the possibility of clearly improving the ergonomics and the efficiency of the injection and suction of the fluids in the vial to be perforated 3. Indeed, during use, the vial to be perforated 3 and the interfacing device 1 are turned upside down, so that the vial 3 is found above the interfacing device 1, as illustrated in FIG. 1. As the fluids are more dense than the gases, the latter flow down therefore towards the plug 3*a* so that the distal orifice 42, which is located in the distal portion 40*b* of the means for circulating fluids, is found in the region of the vial to be perforated 3 comprising the gases, while the proximal orifice 11 is immersed in the fluid.

According to an embodiment, the means for circulating fluids 10, 40 comprise an end piece 10, attached at the proximal end 21*a* of the first conduit 21 of the base 20, and a tube 40, housed in the first 21 and second 22 conduits of the base 20.

The proximal orifice 11 of the means for circulating fluids is formed in a proximal end of the end piece 10, while the distal orifice 42 is formed at a distal end of the tube 40.

The end piece 10 is configured so that, when the base 20 is attached on the vial to be perforated 3, the proximal orifice 11 is located in the internal volume of the vial to be perforated 3. Moreover, the tube 40 may be translationally movable in the first 21 and second 22 conduits of the base 20, in order to adjust the position of the distal orifice 42 according to the volume of the vial to be perforated 3.

Here, the end piece 10 is coaxial with the first 21 and second 22 conduits, and is adapted for receiving the tube 40 in a sliding way. For this, the end piece 10 comprises a passage coaxial with the first and second 22 conduits, said passage opening at a distal end 10*b* of the end piece 10 through a distal hole 12 through which the tube 40 may protrude.

In the embodiment illustrated in the figures, the end piece 10 is of a global cylindrical shape.

Figure 2:
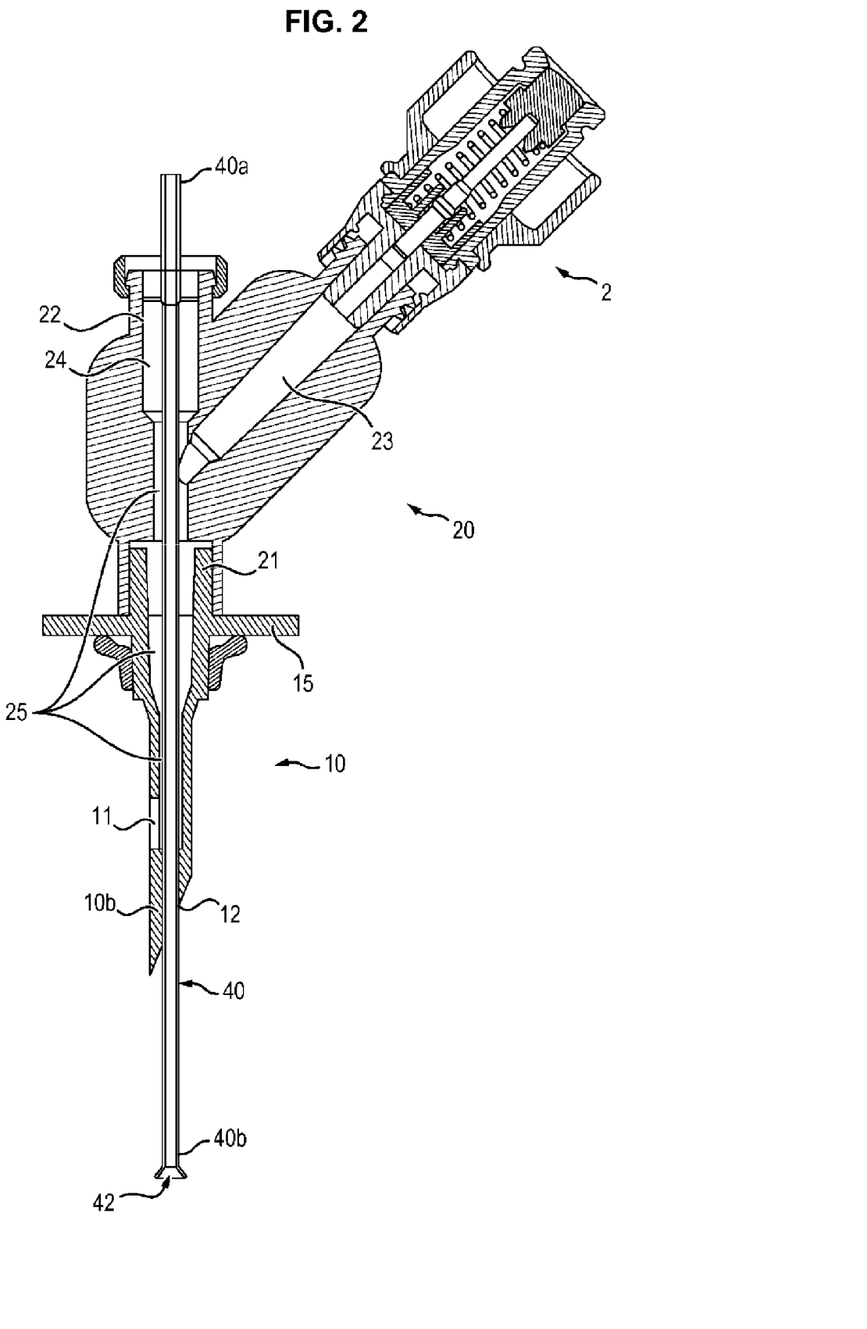
FIG. 2 illustrates a sectional view of the interfacing device of FIG. 1.

Preferably, the tube 40 is dimensioned so as to form a space 25 with internal walls of the conduit 21 and of the end piece 10, so as to allow the passing of the fluids between the proximal orifice 11 and the fluid-injection device 2 (FIG. 2). For example, this passage may extend from the proximal orifice 11, and then run along the tube 40 inside the end piece 10 and of the first conduit 21 in order to open into the third conduit 23.

Advantageously, the space does not communicate with the second conduit 22, which is dedicated to gas exchanges with the vial to be perforated 3 via the tube 40. For this, the second conduit 22 may notably be sealed by means of a sleeve 24, housed in the proximal end 22*a* of the second conduit 22 and configured so as to allow the passing and the translational movement of the tube 40 in the first 21 and second 22 conduits, while preventing the passing of fluids from the fluid-injection device 2 or from the vial to be perforated 3. For example, the sleeve 24 may be of a shape mating the internal wall of the second conduit 22 and be crossed by a central hole, coaxial with the axes X1 and X2 of the first 21 and second 22 conduits and configured for sealably receiving the tube 40. For this purpose, the sleeve 24 may notably be made in an elastomeric material.

In the exemplary embodiment illustrated in the figures, the second conduit 22 is constricted in the proximal portion 22a in order to form an abutment for the sleeve 24 and to fix it in translation. Thus, the space 25 is sealed at the second conduit 22 by the sleeve 24 and the tube 40, deviating the fluids from the proximal orifice 11 to the third conduit 23.

It will be noted that, in this embodiment, the proximal orifice 11 may be in a side wall of the end piece 10 and open into the passage 25. Advantageously, the proximal orifice 11 then extends into an area very close to the plug 3a, which increases the amount of fluids which may be absorbed.

Alternatively, the role of the proximal orifice 11 may be held by the distal hole 12 of the end piece 10, which is crossed by the tube 40, the distal orifice 42 remaining at the distal end 40b of the tube 40.

The distal end 40b of the tube 40 may have a suitable flaring for preventing the extraction of the tube 40 of the vial to be perforated 3. For example, when the tube 40 is translationally movable in the distal orifice 12 of the end piece 10, the flaring is laid out so as to come into abutment against the walls forming the distal orifice 12. In this embodiment, the gas intake may therefore be accomplished from the distal orifice 42 of the end piece 10 as far as the bottom wall of the vial 3 (under the assumption that the length of the tube 40 is sufficiently long for reaching this wall). The initially present gas in the vial to be perforated 3 may therefore freely circulate and in a closed circuit, notably when a tank 31 is sealably connected to the second conduit 22.

Thus, the proximal orifice 11 of the end piece 10, used for the fluid intake, is located in proximity to the plug 3a, while the distal orifice 42 used for the intake of gas, may be located in any point between the distal orifice 12 of the end piece 10 and the bottom of the vial to be perforated 3, when the tube 40 is translationally mobile. The air and fluid intakes are therefore spatially de-correlated.

The tube 40 may notably be in stainless steel.

The end piece 10 may be configured for perforating the vial to be perforated 3. For this purpose, the distal end 10b of the end piece 10, through which passes the tube 40, may be conformed so as to cross the plug 3a of the vial to be perforated 3 in a sealed way. Typically, the distal end 10b of the end piece 10 may be point-shaped.

Alternatively, the perforation may be accomplished by means of the tube 40, of a perforator distinct from the end piece 10 or from any other suitable means.

Moreover, in order to retain the end piece 10 in position inside the vial to be perforated 3, the latter may comprise, in an intermediate area extending between the proximal orifice 11 and the first conduit 21 of the base 20, retention means, preferably in an area adjacent to the proximal orifice 11 so that the latter remains permanently inside the vial 3.

For example, the retention means may comprise fins 13, having a divergent proximal end forming a shoulder 13a suitable for abutting against the plug 3a of the vial 3 and thus preventing the extraction of the interfacing device 1. Moreover, the fins 13 may further comprise a convergent distal end 13b facilitating the penetration of the end piece 10 into the vial 3. In order to limit the deterioration of the plug 3a, the end piece 10 preferably comprises between two and four fins 13.

Figure 4A:
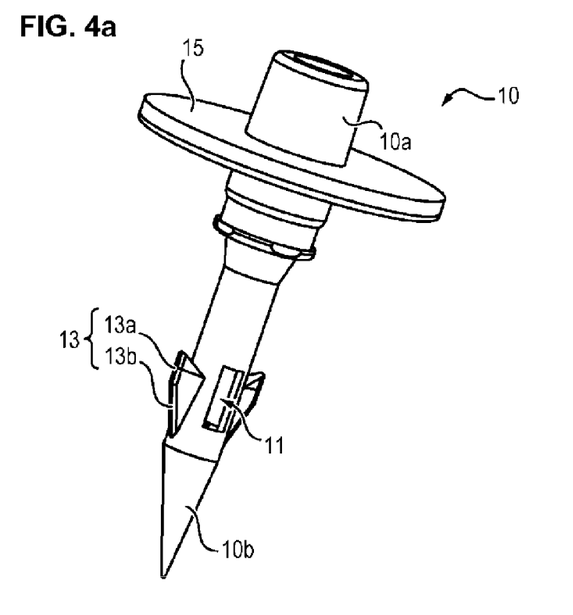
FIGS. 4a and 4b illustrate perspective views of the end piece of the interfacing device of FIG. 1.
Figure 4B:
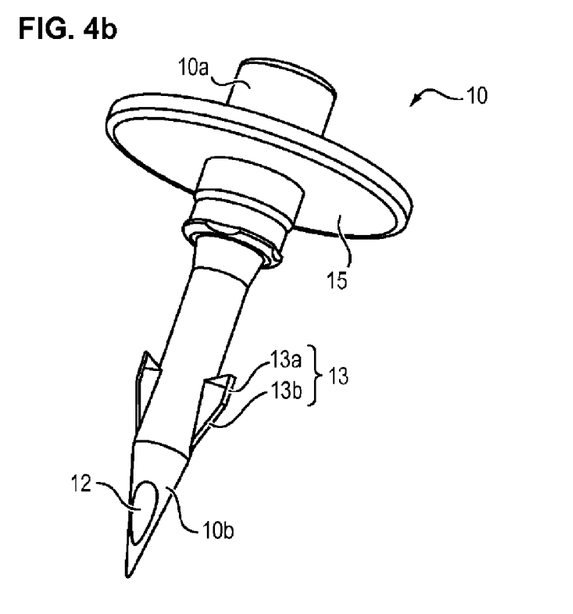

In the illustrated embodiment in the figures, the proximal orifice 11 is formed between two of the fins 13. Thus, even when the shoulder 13a will abut against the plug 3a, the fluidic communication between the vial 3 and the proximal orifice 11 is maintained (FIGS. 4a, 4b).

In order to facilitate suction of the gas and of the fluid, the operator may notably cause the end piece 10 to pivot in the plug 3a of the vial to be perforated 3. The connection between the end piece 10 and the plug 3a of the vial to be perforated 3 is actually of the ball-joint type because of the flexibility of the plug 3a and the shape of the end piece 10, and therefore gives the possibility to the operator of accessing the whole of the internal volume of the vial 3.

The proximal end of the end piece 10 comprises a disc 15 extending transversely to the axis X1 and configured for extending outside the vial to be perforated 3 in order to facilitate gripping of the interfacing device 1, in particular during the insertion S2 of the end piece 10 through the plug to be perforated 3a.

The end piece 10 may be entirely formed and in a single part, notably in plastic, with the first conduit 21 of the base 20, or alternatively be added onto the distal end 21b of the first conduit 21 and then made secured to the latter, by adhesive bonding, welding or any other suitable means.

According to an alternative embodiment (not illustrated in the figures), both the proximal orifice 11 and the distal orifice 42 are formed in the end piece 10. The end piece 10 is then configured so that, when the base 20 is attached on the vial to be perforated 3, both orifices 11, 40b are located in the internal volume of the vial to be perforated 3. In this alternative embodiment, the end piece 10 then comprises a dedicated channel for the gases, which opens at the distal orifice 42, and a dedicated channel for the fluids, which opens at the proximal orifice 11.

Alternatively (not illustrated in the figures), the proximal orifice 11 and the distal orifice 42 may be formed in two distinct and separate channels, each attached to the base 20 and in fluidic communication with the corresponding conduit of said base 20.

The Gas Exchange Device

The interfacing device 1 may notably comprise a gas exchange device 30, such as a tank 31 or a filter, connected to the proximal end 22a of the second conduit 22 via an attachment base 32. In use, the gas exchange device 30 is in fluidic communication with the tube, in order to circulation of the gases from the vial to be perforated.

More specifically, the attachment base 32 may comprise a suitable housing for sealably receiving the proximal end 40a of the tube 40 while allowing fluidic communication between the tube 40 and the gas exchange device 30. The attachment base 32 may notably be made in a plastic material.

The second conduit 22 may notably comprise, at its proximal end 22a, snap-on fastening means suitable for cooperating with the attachment base 32 and for maintaining it in position.

Figure 7A:
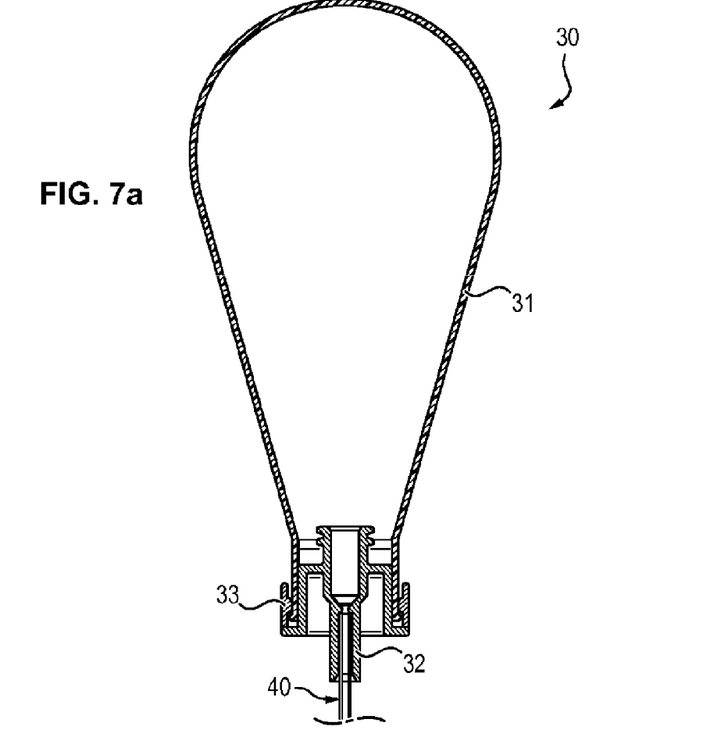
FIGS. 7a and 7b illustrate sectional views of two embodiments of the gas-exchange device which may be used in the interfacing device according to the invention.

According to a first embodiment, the gas exchange device 30 is a tank 31 comprising an elastomeric vial (FIG. 7a), attached to the attachment base 32 through a holding ring 33. Notably reference will be made to document FR 2 982 484 in the name of the Applicant for more details on this type of tank. In this embodiment, the vial 31, the attachment base 32 and the holding ring 33 are secured to the tube 40, for example by adhesive bonding. Preferably, the main axis of the vial 31 extends in the extension of the tube 40, i.e. along the axis X2 and if necessary the axis X1, for balancing and ergonomic reasons (FIG. 7a).

Figure 7B:
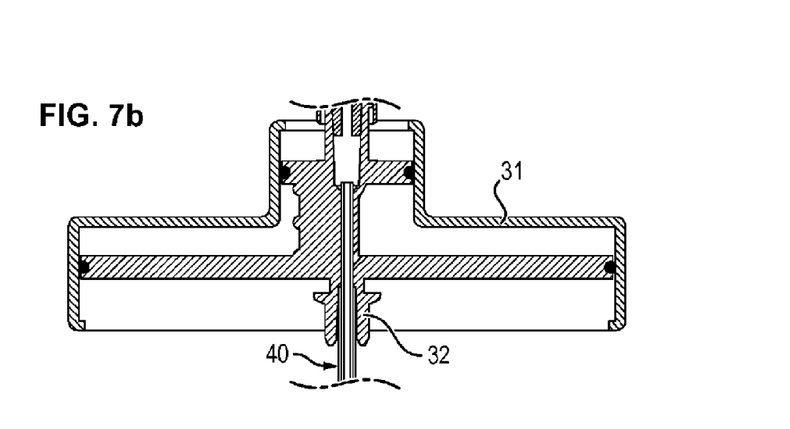

According to a second embodiment, the gas exchange device 30 may include a rigid tank 31 with a variable volume or a case. The case also has an attachment base 32 which connects the proximal end 40a of the tube 40 to the tank 31 sealably. Here again, reference may be made to document FR 2 982 484 in the name of the Applicant for more details (FIG. 7b). Advantageously, as such a tank 31 is rigid, it does not have the risk of being accidentally perforated during its storage or its handling by an operator.

The Protective Member

In order to avoid that the operator comes into contact with possible drops of the product contained in the vial to be perforated 3, the interfacing device 1 may comprise a protective member 60, which may be attached on the vial to be perforated 3 so as to extend between the plug 3a and the base 20.

The protective member 60 may for example comprise a protective sachet, which may be attached to the base 20 on the one hand, and to the vial to be perforated 3 on the other hand. For this, the protective sachet 60 may for example be securely attached at the first conduit 21 of the base 20 and comprise an elastic attachment means, suitable so as to be fitted onto the plug 3a and to engage into an underlying area of the latter.

Gripping means 61 may be attached to this sachet, typically in an area adjacent to the elastic attachment means for the sachet 60.

Figure 6:
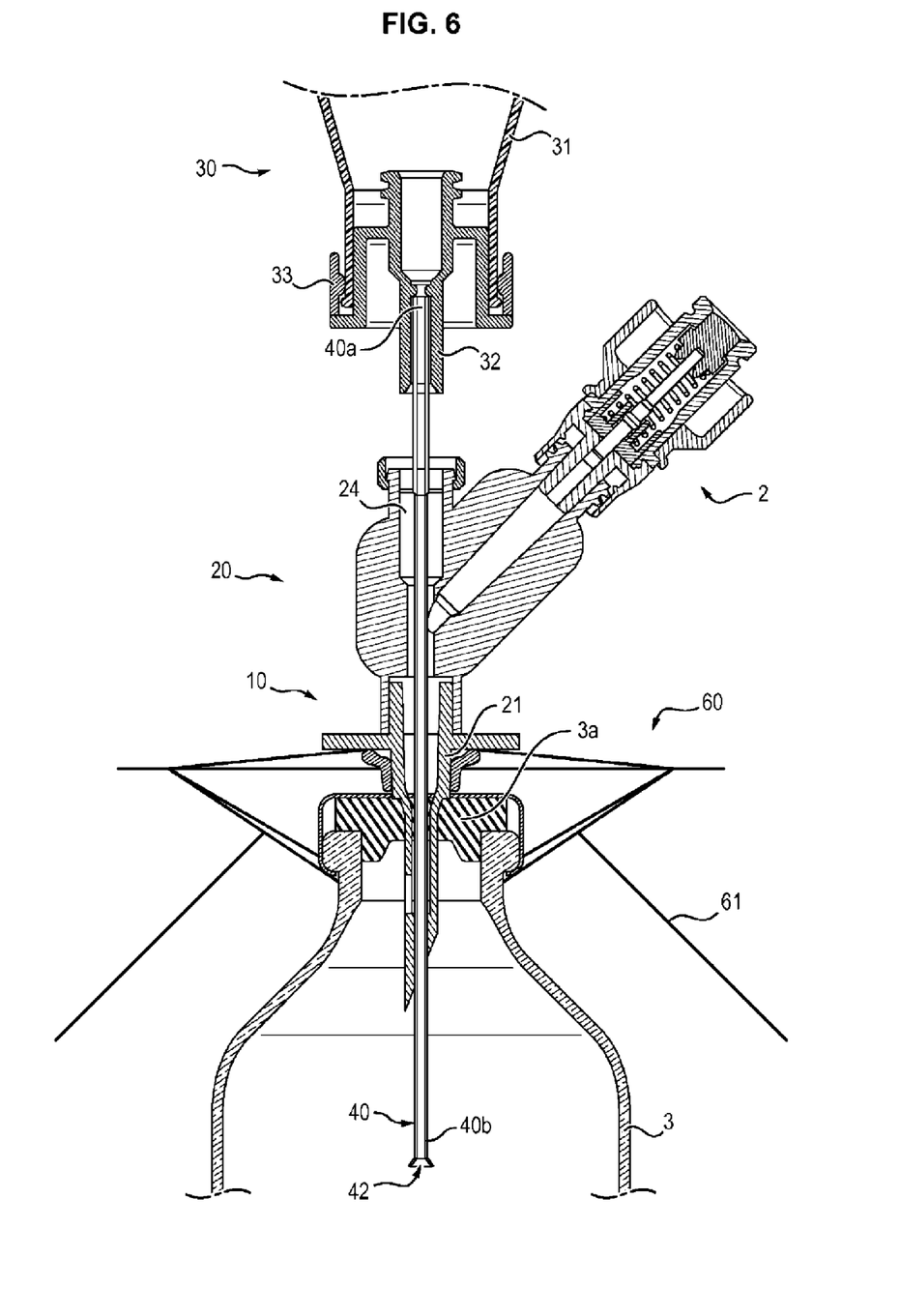
FIG. 6 illustrates a sectional view of the interfacing device of FIG. 1, provided with a protective member.

Once the interfacing device 1 is attached on the vial to be perforated 3, the protective sachet 60 therefore covers the whole portion of the interfacing device 1 extending between the plug 3a and the area of the base 20 in which is attached the sachet 60, thus preventing any contact between the contents of the vial to be perforated 3 and the operator (FIGS. 1 and 6).

Method of Use

Now we shall describe a method S for using an interfacing device 1 according to the invention.

In the following, we shall more particularly describe the use of an interfacing device in which the first 21 and second 22 conduits of the base 20 are substantially parallel and aligned and receive a translationally movable tube 40. Moreover, in the following, the interfacing device 1 comprises a tank 31, as a case, and the end piece 10 plays the role of a perforator.

However, this is not limiting since, as indicated above, the interfacing device 1 does not necessarily comprise a translationally movable tube 40 in the first 21 and second 22 conduits, nor any tank of the case type 31 (which may quite be replaced with a filter or an elastomeric vial). Moreover, the role of the perforator may be played by a part other than the end piece 10.

Here, the vial to be perforated 3 contains a product as a powder and an inert gas. One skilled in the art will however be able to easily adapt this method to a vial to be perforated initially containing a fluid or powder in vacuo, the only difference lying in the fact that the vial to be perforated 3 does not initially comprise a gas which has to be discharged into the tank 31.

Figure 8:
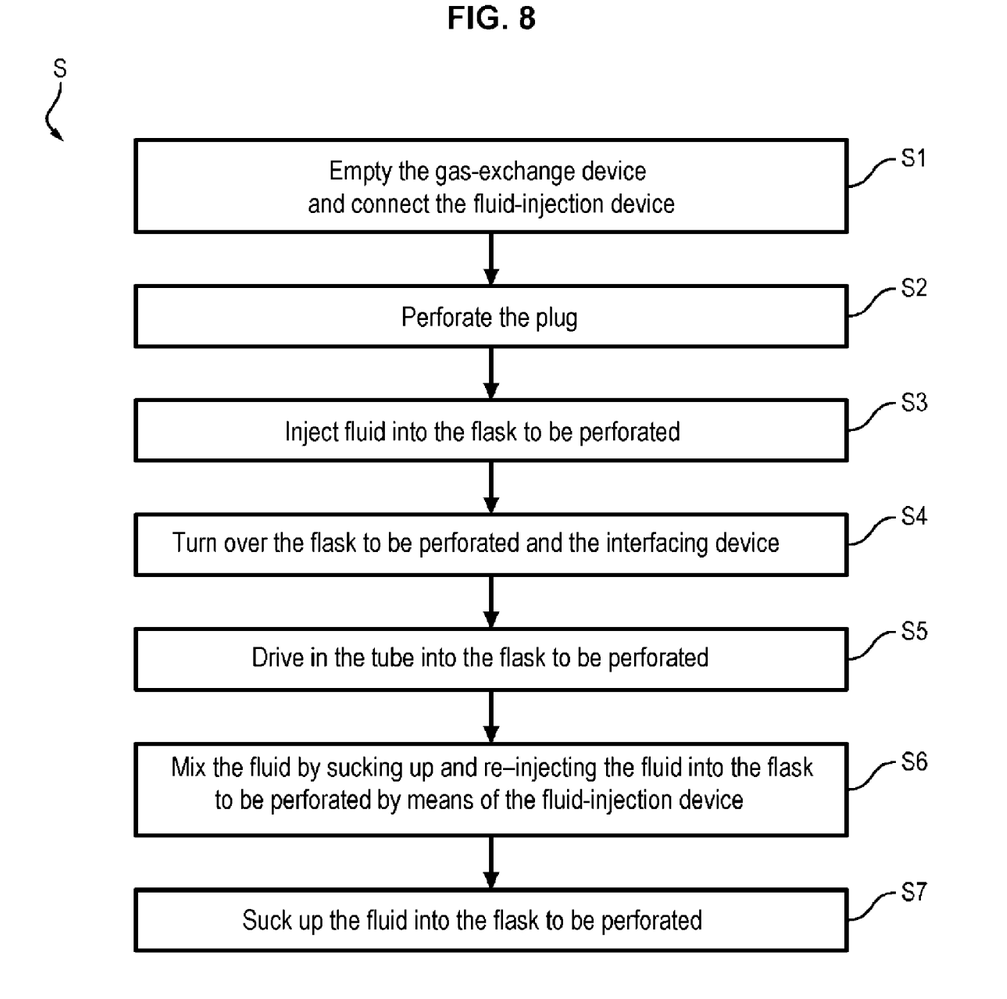
FIG. 8 is a flow chart illustrating various steps of an exemplary embodiment of the method of use of an interfacing device according to the invention.

During a first step S1, the operator drives out the gas contained if necessary in the tank 31 and connects the fluid-injection device 2 to the third conduit 23 of the base 20, by ensuring preferably avoidance of any drop formation for limiting the risks of contamination, and then the operator injects the fluid into the vial to be perforated 3.

In the case when the third conduit 23 of interfacing device 1 is sealed by means of a membrane, it will be understood that the connection of the fluid-injection device 2 to the base 20 may be achieved following the step S2 for perforating the vial to be perforated 3.

Figure 3:
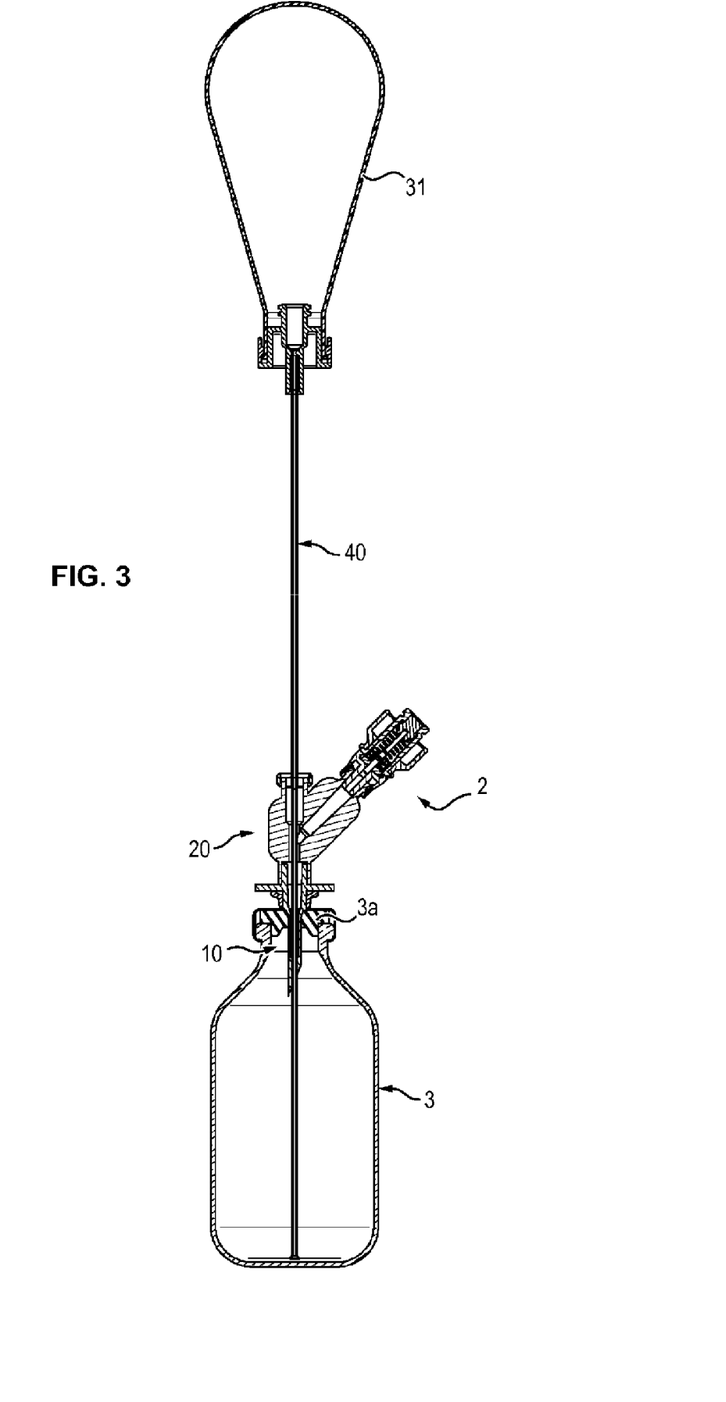
FIG. 3 illustrates a sectional view of the interfacing device of FIG. 1, in its position of introduction into the vial.

During a second step S2, the operator may then perforate the plug 3a of the vial 2 by pushing the pointed distal portion 10b of the end piece against the plug 3a. In order to facilitate this perforation, the vial to be perforated 3 may be laid vertically on a support, the neck upwards, and the end piece 10 may be driven into the plug 3 from the top downwards. For this operation, the distal end 40b of the tube 40 is preferably placed in abutment against the distal orifice 12 of the end piece 10, in order not to damage the tube 40 (FIG. 3).

Advantageously, the sleeve 24 seals the second conduit 22 while the membrane seals the third conduit 23, thereby avoiding passing of gas if necessary loaded with powder initially contained in the vial to be perforated 3.

During a third step S3, the operator injects fluid into the vial to be perforated 3.

The injection of fluid into the vial to be perforated 3 has the effect of driving out the initially present gas in the vial to be perforated 3 towards the tank 31, the internal volume of which then increases in proportion to the received volume of gas.

During a fourth step S4, the operator may then turn over the assembly so as to position the fluid-injection device 2 vertically, the vial to be perforated 3 above the interfacing device 1, so that the proximal orifice 11 for fluid intake is then immersed (FIG. 1, without any fluid-injection device 2).

Moreover, the configuration of the base 20 (first conduit 21 and second conduit 22 extend in the extension of each other, the third conduit 23 extending obliquely) makes the handling of the interfacing device 1 more ergonomic and easy: it is actually possible to position the interfacing device 1 and the vial to be perforated 3 so that the third conduit 23 substantially extends vertically, thereby facilitating suction and introduction of the fluids into the vial to be perforated 3 by means of the injection device 2. Moreover it is recalled that the mechanism for filling or purging the tank 31 is carried out in a passive way, i.e. without any intervention of the operator, by simple adjustment of the internal pressure of the tank 31 and of the vial to be perforated 3.

During a fifth step S5, the operator may drive in the tube 40 into the vial to be perforated 3 so as to bring the distal orifice 42 into the area of the vial to be perforated 3 containing the gases, i.e. towards the bottom of the latter.

Thus, the proximal orifice 11 is immersed in the fluid, while the distal orifice 42 is brought into the area occupied by the gases, which allows efficient de-correlation of both fluid intakes.

Advantageously, the ball-joint effect allowed by the plug 3a gives the possibility of bringing the distal orifice 42 into any point of the vial to be perforated 3.

During a sixth step S6, the operator may mix the liquid and the powder of the contents of the vial to be perforated 3 by sucking up and then re-injecting several times by means of the injection device 2, the fluid loaded with product, so as to solubilize the product initially as a powder in the fluid and of homogenizing it. If need be, the operator may cause the shoulders 13a to abut against the plug 3a in order to further bring the proximal orifice 11 closer to the fluid intake of the plug 3a.

During this step S6,
 the distal orifice 42 remains outside the fluid, which gives the possibility of avoiding the generation of bubbles in the fluid or of losing fluid in the tank 31 via the intermediate tube 40,
 the proximal orifice 11 is located in proximity to the plug 3a of the vial to be perforated 3, which gives the possibility of substantially taking up all the fluid.

This overturn position is more ergonomic for the operator and less tedious, in particular when the fluid is viscous. The center of gravity of the system is actually quite close to the axis of the fluid-injection device 2. The ergonomics and the practicality of this overturn position are made possible by means of the angle α between the axis X2 of the second conduit 22 and the axis X3 of the third conduit 23 which is preferably comprised between 30 and 60°. Indeed, gravity is thus utilized for more easily sucking up the fluid.

Further, the fluid-injection device 2 is made secured to the vial to be perforated 3 via the end piece 10 and the base 20, which greatly simplifies its handling.

Alternatively, the operator may again turn over the interfacing device 1 for re-injecting the fluid into the vial to be perforated 3, in order to thus again make use of gravity. For this, the operator may also cause the tube 40 to pump back into abutment with the distal end 10b of the end piece 10. Practically, if the need is perceived at the handling, the operator may use the interfacing device 1 in a normal position, i.e. a vial to be perforated 3 downwards every time when it is desired to inject liquid into the vial to be perforated 3 and then in an overturn position, i.e. a vial to be perforated 3 at the top and a tube 40 in abutment against the bottom of said vial 3, every time suction of the liquid from the vial to be perforated 3 is desired.

By means of the sachet 60 forming the protective member, the operator is protected from possible drops which may leak between the end piece 10 and the plug 3a, notably in the case of a plug 3a of poor quality or deteriorated, or of a poor handling of the interfacing device 1.

Next, after having satisfactorily diluted the product, during a step S7, the operator may suck up the desired volume of fluid in this overturn position, and then, after having put the system back into a normal position, detach the fluid-injection device 2 from the interfacing device 1.

Naturally, the present invention is by no means limited to the embodiments described above and illustrated in the drawings, but one skilled in the art will be able to provide it with many alternatives and modifications.

The invention claimed is:

1. An interfacing device intended to establish a connection between a fluid-injection instrument and a vial to be perforated, comprising:
   a base comprising:
   a first conduit, suitable for being attached to the vial to be perforated,
   a second conduit suitable for allowing circulation of gases in the vial to be perforated, and
   a third conduit suitable for being connected to the fluid-injection instrument,
   means for circulating the fluids, comprising a proximal orifice in fluidic communication with the third conduit, wherein said means for circulating the fluids further comprise a tube, housed in the second conduit and translationally movable in said second conduit, said tube comprising at its distal end a distal orifice in fluidic communication with the second conduit, the proximal orifice and the distal orifice being configured for opening into the vial to be perforated when the interfacing device is attached to said vial to be perforated,
   said interfacing device further comprising a gas exchange device including at least one of a filter or a tank attached to a proximal end of the tube, wherein said gas exchange device is in fluid communication with the tube in order to allow circulation of the gases from the vial to be perforated.

2. The device according to claim 1, wherein the distal end of the tube is flared.

3. The device according to claim 1, wherein the means for circulating the fluids comprise an end piece, attached at a distal end of the first conduit of the base, said end piece comprising at its proximal end the proximal orifice.

4. The device according to claim 3, wherein the tube is housed in the end piece and is translationally movable in said end piece.

5. The device according to claim 3, wherein the proximal end is formed at a proximal end of the end piece.

6. The device according to claim 3, wherein a distal end of the end piece is pointed.

7. The device according to claim 1, wherein the proximal orifice laterally extends relatively to an extension direction of the tube.

8. The device according to claim 1, further comprising a sleeve positioned in the second conduit and suitable for sealingly maintaining the tube in said second conduit.

9. The device according to claim 1, further comprising a protective member, attached on the first conduit and suitable for being attached to the vial to be perforated.

10. The device according to claim 1, wherein the first conduit and the second conduit are coaxial, the third conduit forming an angle comprised between 30° and 60° with the second conduit.

* * * * *